(12) United States Patent
Chawla

(10) Patent No.: US 8,242,447 B1
(45) Date of Patent: Aug. 14, 2012

(54) METHOD AND APPARATUS FOR DETECTING EXPLOSIVES USING DIFFERENTIAL INVERSE HILBERT SPECTROSCOPY FACILITATED BY A HIGH TEMPERATURE SUPERCONDUCTING QUANTUM SYSTEM

(75) Inventor: Manmohan S. Chawla, University Park, MD (US)

(73) Assignee: System Planning Corporation, Arlington, VA (US)

( * ) Notice: Subject to any disclaimer, the term of this patent is extended or adjusted under 35 U.S.C. 154(b) by 67 days.

(21) Appl. No.: 12/862,719

(22) Filed: Aug. 24, 2010

(51) Int. Cl.
*G01J 1/00* (2006.01)
(52) U.S. Cl. .................. 250/336.1; 250/338.1
(58) Field of Classification Search ..... 250/336.1–338.1
See application file for complete search history.

(56) References Cited

OTHER PUBLICATIONS

Divin et al., "Hilbert Spectroscopy of Liquids for Security Screening," Detection of Liquid Explosives and Flammable Agents in Connection with Terrorism, NATO Science for Peace and Security Series B: Physics and Biophysics, 2008, 189-204.*
Gray et al., "Emission of Terahertz Waves From Stacks of Intrinsic Josephson Junctions," IEEE Transactions on Applied Superconductivity, vol. 19 (3), p. 886-890, Jul. 2009.*
Divin et al., "High-Tc Josephson Square-Law Detectors and Hilbert Spectroscopy for Security Applications," IEEE Sensor Journal, 8 (6), pp. 750-757, Jun. 2008.*

* cited by examiner

*Primary Examiner* — David Porta
*Assistant Examiner* — Casey Bryant

(57) ABSTRACT

An apparatus and method designed for generating and detecting reflected Terahertz waves using high-transition temperature (Tc) superconducting quantum devices (Josephson junctions) is described and the spectral response of reflected Terahertz radiation is mathematically analyzed to positively identify explosives strapped on a human or animal subject. This embodiment is well-suited for high traffic physical locations currently under surveillance such as security check points and also venues demanding significantly less obtrusive surveillance such as revolving entry doors, moving walkways, and entry gates of an airplane. The apparatus and method detects explosives through clothing without raising privacy concerns.

3 Claims, 10 Drawing Sheets

| Explosive | Spectral Line Voltage (mV) | | | | | | |
|---|---|---|---|---|---|---|---|
| TNT | 3.43 | 4.55 | 7.63 | 9.74 | 11.41 | | |
| RDX | 1.70 | 2.17 | 3.10 | 4.05 | 4.55 | 6.37 | 13.92 |
| HMX | 3.68 | 5.19 | 5.83 | 10.98 | 12.53 | | |
| PETN | 4.14 | 5.87 | | | | | |
| Tetryl | 12.34 | | | | | | |
| Aspirin | 2.85 | 6.74 | | | | | |
| Lactose | 1.12 | 2.48 | 2.85 | 3.76 | 5.25 | 5.93 | 6.80 |

FIG. 4

METHOD AND APPARATUS FOR DETECTING EXPLOSIVES USING DIFFERENTIAL INVERSE HILBERT SPECTROSCOPY FACILITATED BY A HIGH TEMPERATURE SUPERCONDUCTING QUANTUM SYSTEM

BACKGROUND OF THE INVENTION

1. Field of the Invention

The present invention relates to a device and method for detecting explosives. More particularly, the present invention relates to an apparatus and method for generating and detecting Terahertz radiation to positively identify explosive devices carried on human or animal subjects.

2. Description of Related Art

The purpose of this invention is to address privacy concerns that plague the millimeter waver/Terahertz imagers that are being installed in various U.S. and international airports. The current full body imagers can detect explosives using millimeter and Terahertz waves directed against clothing or packing material. However, privacy concerns persist due to the inevitable picturing and highlighting of human body parts.

It is well known that organic molecules have unique vibrational and rotational frequencies and that the rotational frequencies lie in the Terahertz regime. The Terahertz waves also have the capability to excite these rotational frequencies within the molecules of explosive materials. The commonly used explosive RDX, for example, has spectral lines at 0.82, 1.05, 1.50, 1.96, 2.20, 3.08 and 6.73 THz. A simultaneous detection of these rotational frequencies or wavelengths, through several layers of clothing, will constitute a very robust detection of RDX. Other explosives can be similarly detected. In addition to spectral specificity, good imaging resolution is inherently possible as the wavelengths associated with Terahertz, 15 μm to 1 mm, are short. However, privacy concerns still exist in this kind of imaging hence imaging will not be attempted.

The role Terahertz frequencies can play in the detection of explosives has been well known for some time. However, it has been difficult to make robust THz sources or detectors. Terahertz frequencies (0.5 to 5.0 THz) occupy the region of electromagnetic spectrum that is sandwiched between microwaves and infrared, and these frequencies are too high to be produced by conventional electronics and too low to be produced by solid state lasers. The conventional sources of THz are ultra-fast laser switches, pumped gas lasers, optical difference generation techniques, frequency doubling diodes and quantum cascade lasers. All of these require cumbersome equipment and large power sources.

Other detection systems like the Ion Mobility Spectrometer require a small sample of the explosive to be physically brought to the machine for analysis. In the end, none of the prior art discloses an effective and efficient way to detect explosives. Therefore, a need exists to develop a novel alternative that can detect and positively identify explosives in real time without the drawbacks evident in the prior art.

SUMMARY OF THE INVENTION

The object of the present invention is to overcome the shortcomings disclosed in the prior art. The technique of the present invention is based on illuminating human subjects, one at a time or in groups, by very low power Terahertz waves and then looking for the spectral signatures or the fingerprints of explosives in the reflected energy. Most explosives are translucent to the Terahertz frequencies; transmitting some frequencies, reflecting other frequencies and absorbing yet others frequencies. Accordingly, the reflected spectrum will show features corresponding to the lines that were absorbed while operating in the transmission mode, specifically the reflected spectrum will be complementary to the absorbed spectrum.

According to a further aspect of the present invention, detecting explosives through clothing without raising privacy concerns is facilitated by high-transition temperature ($T_c$) superconducting Josephson junctions that generate Terahertz waves as well as detect the reflected Terahertz waves. According to a further aspect of the present invention, real time explosive fingerprints can be derived from the information contained in the reflected waves using innovative mathematical techniques. According to a still further aspect of the present invention, a plurality of Josephson junction source/detector combinations can be incorporated in the revolving entry doors of airports, moving walkways, security check points, jetways and the entry gates of the airplanes so that explosive material carried on a human subject can be detected at several observation points.

The accompanying drawings, which are incorporated in and constitute part of the specification, illustrate various embodiments of the invention and together with the description, serve to explain the principles of the invention.

BRIEF DESCRIPTION OF THE DRAWINGS

FIG. 4 shows a table of voltage specific signatures of common explosives.

DESCRIPTION OF THE PREFERRED EMBODIMENTS

Figure 1:
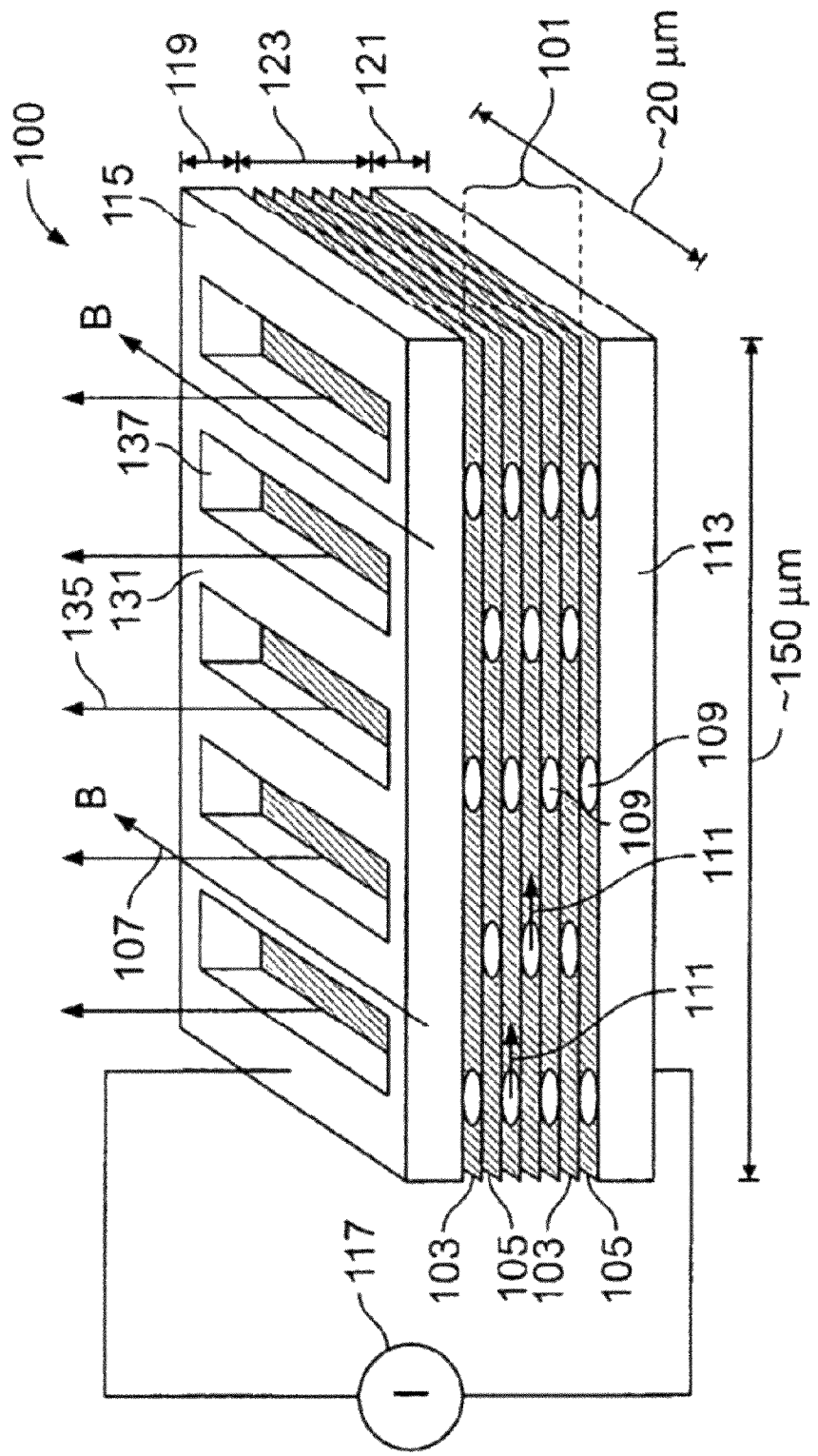
FIG. 1 shows an example of a high temperature superconducting Josephson junction stack as known in prior art.

For the purposes of promoting an understanding of the principles of the invention, reference will now be made to the embodiments illustrated in the drawings and specific language will be used to describe the same. It will nevertheless be understood that no limitation of the scope of the invention is hereby intended and such alterations and further modifications in the illustrated devices are contemplated as would normally occur to one skilled in the art.

According to the present invention, a high-transition temperature ($T_c$) superconducting Josephson junction stack is provided to generate THz frequencies. As shown in FIG. 1, an example of a high-transition temperature ($T_c$) superconducting Josephson junction stack is disclosed. The detailed operation of an exemplary Josephson junction stack is further detailed in U.S. Pat. No. 7,610,071 to Welp et al., which is hereby incorporated by reference. As shown in FIG. 1, an exemplary Terahertz emitter includes stacks 101 of superconducting layers 103 and insulating layers 105. These layers 103, 105 are disposed between a top metal layer 115 and a bottom metal layer 113. The metal layers are generally gold or gold alloy.

In a preferred embodiment of the present invention, the source of the electromagnetic energy is a single crystal superconductor $Bi_2Sr_2CaCu_2O_8$ (BSCCO) which is comprised of layers 103 and 105. The superconducting layers 103 are composed of superconducting $CuO_2$-planes that are coupled to each other across the intervening insulating BiO—SrO layer portions 105 though weak Josephson coupling.

When subjected to an applied magnetic field, B, denoted by 107 oriented parallel to the planes, the magnetic field lines will penetrate the material in the form of Josephson vortices 109 that squeeze in between the superconducting layers 103. The centers of the Josephson vortices 109 reside in the insulating layer portions 105. A current, I, denoted by 117 flows perpendicular to the planes down the stack of the layers (103) and also the insulating layers 105. The resulting current flow generates a Lorentz force that drives the Josephson vortices 109 parallel to the planes in a direction denoted as 111 at high velocities. This coherently moving Josephson vortex 109 induces electromagnetic waves and currents. Their frequency, f, is determined by the voltage, V, across the applied current.

The layered superconducting structure of the device 100, as shown in FIG. 1, exhibits a spectrum of electromagnetic modes, the Josephson plasma waves, which are analogous to the guided modes in a waveguide. If the applied field and current are adjusted in such a way that the velocity of the moving lattice of the Josephson vortices 109 coincides with that of a Josephson plasma mode, resonance occurs and a large amount of energy is pumped from the moving lattices of the vortices 109 into this plasma wave. The estimated electromagnetic power density in the stack 101 at THz-frequencies is approximately 100 W/cm². In addition, the metal grating 131 will induce a strong periodic variation of the dielectric constant at the surface of the superconducting stack 101. THz radiation 135 will thereby be emitted through the slots 137 in the grating realizing the so-called 'surface-emitting configuration.' This configuration significantly enhances the active surface area, and thereby greatly increases the radiated power thereby allowing the steering of a coherent THz beam for imaging applications such as those of the present invention. Steering of the emitted THz beam is accomplished by tuning the Josephson vortex spacing around the grating period using a superimposed magnetic control field.

The relationship between frequency and applied voltage is given by $f=K_J V$, where $K_J = 2e/\hbar$ is a material constant with a value of $4.84 \times 10^{14}$ Hz/Volt for BSCCO material. By changing the voltage from 1 mV to 10 mV, a range of frequencies, 0.5 THz to 5.0 THz is obtained. Materials such as $YBa_2Cu_3O_{7-x}$ (YBCO) can also be used instead of BSCCO. The high-temperature superconductors BSCCO and YBCO are similar in many respects except that the transition temperature ($T_c$) of BSCCO ($T_c$ of 110 K) is higher than that of YCBO ($T_c$ of 93 K). Further, BSCCO has an energy gap 38.5 meV while YCBO has an energy gap of 16 meV which means a larger set of frequencies can be generated using BSCCO.

According to a further aspect, the present invention employs the methodology of Inverse Hilbert Transform Spectroscopy which employs a $YBa_2Cu_3O_7$ superconducting Josephson junction detector that operates at high-transition temperatures ($T_c$) representative of liquid nitrogen. This methodology is disclosed in Divin et al., "Terahertz Hilbert Spectroscopy by High $T_c$ Josephson Junctions" Advances in Solid States Phys 41, 301-313 (2001), which is hereby incorporated by reference. In accordance with Divin, if a Josephson junction is irradiated with reflected wave, its electric response H(V), is proportional to the Hilbert Transform of the spectrum S(f). Applying the inverse Hilbert Transform to the measured H(V), the spectrum S(f) can be recovered as follows:

$$S(f) = \frac{1}{\pi} P \int_{-\infty}^{\infty} \frac{H(V_J) DV_J}{V_J - V}$$

where $V_J$ is the voltage developed in the Josephson junction and P stands for Principal value of the integral. Hilbert Transform is similar to Fourier Transform except that the detector is nanometric in size and does not require bulky optical components.

Figure 2:
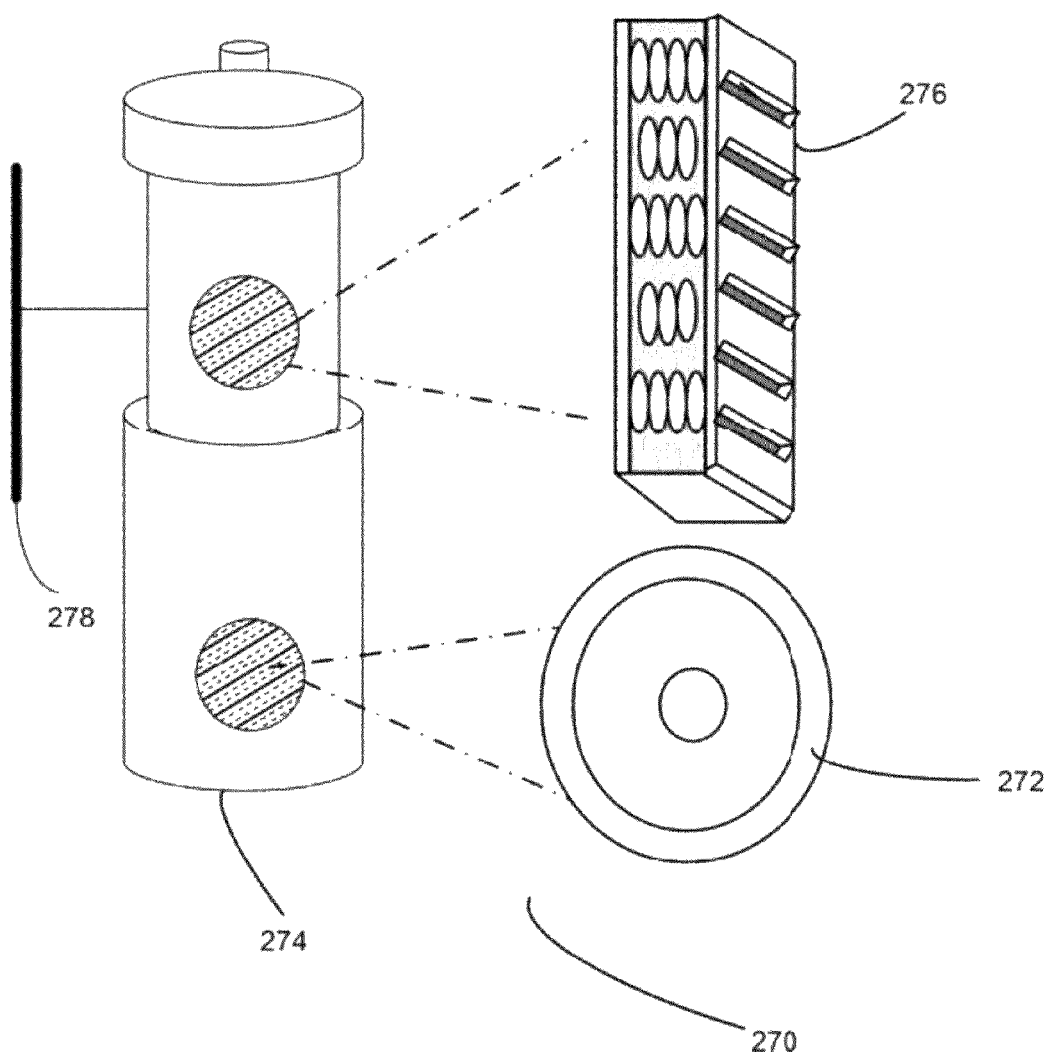
FIG. 2 shows a first preferred embodiment of the present invention.

With reference now to FIG. 2, a preferred embodiment of the present invention 270 will now be discussed. In operation, a liquid nitrogen Dewar 274 contains a BSCCO source 276 and a YBCO detector 272. Each source/detector 276/272 combination captures the spectral response of roughly 0.75 sq. inch of the human body. A computer 278 initiates the powering cycle of each source 276 in a simultaneous or sequential manner from left to right and then from top to bottom. The detector 272 is left unpowered. Each source 276 is powered only for a short time necessary to produce a highly resolved reflected signal from each irradiated element of the subject. Output may be calibrated periodically or just before each spectral session.

Figure 3:
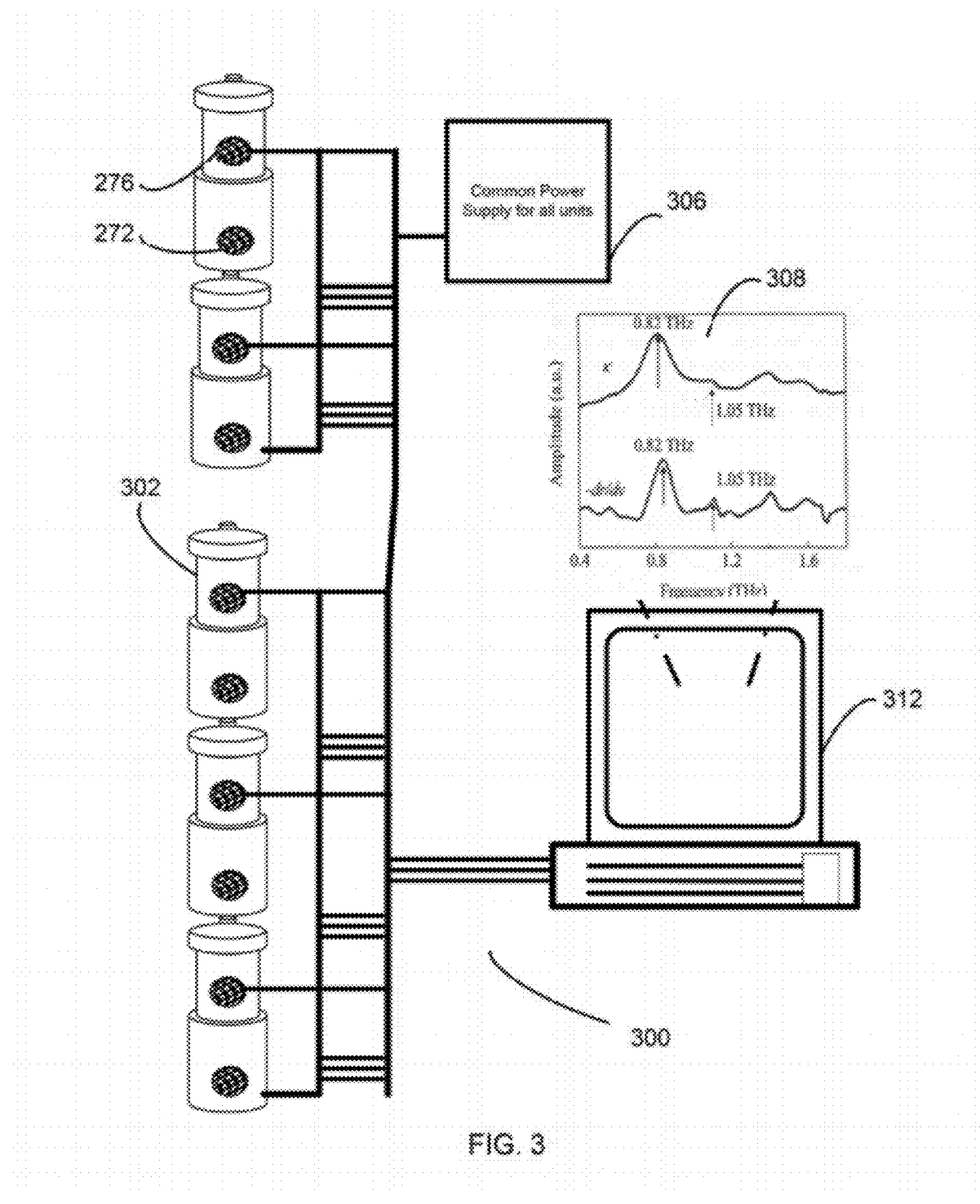
FIG. 3 shows a second preferred embodiment of the present invention.

With reference now to FIG. 3, a functional configuration of a preferred embodiment of the present invention is provided. As shown, a plurality of liquid nitrogen Dewar units 302, each containing a source 276 and/or emitter 272, are connected by a common power source 306 and a computer 312 which will assemble spectral image from each detector 272 and perform inverse Hilbert Transform and differentiate each spectrum to identify explosives through a Terahertz signature 308.

Figure 5A:
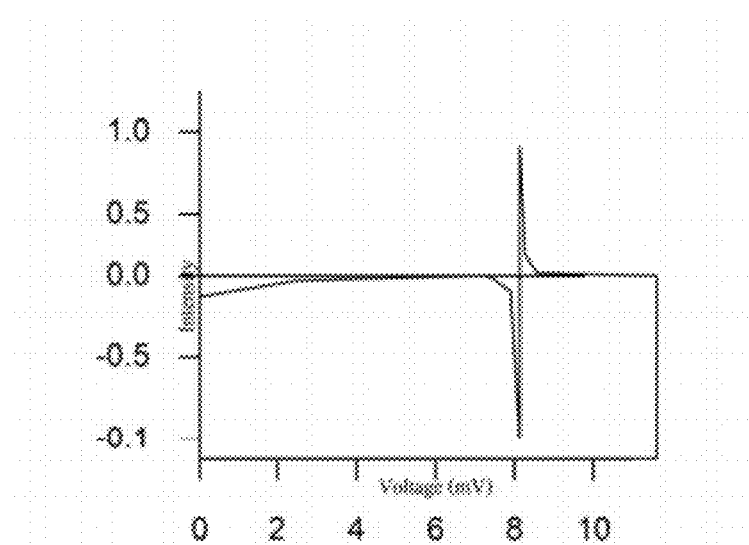
FIG. 5A shows intensity versus voltage graph in the Josephson junction detector.
Figure 5B:
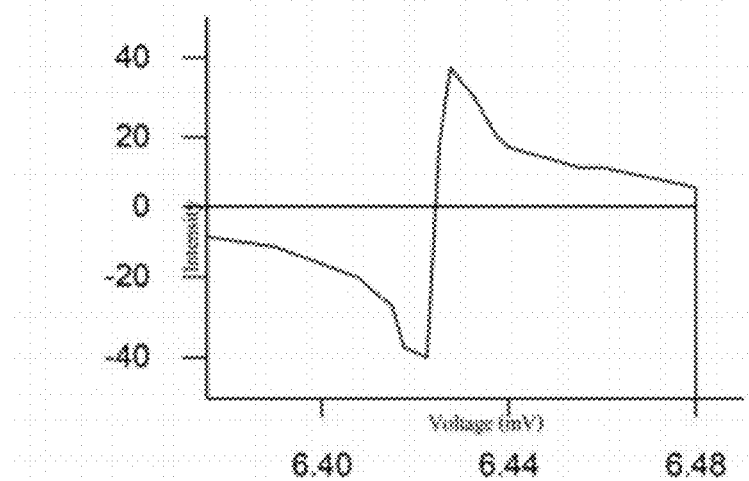
FIG. 5B shows an intensity versus voltage in the Josephson junction detector.
Figure 5C:
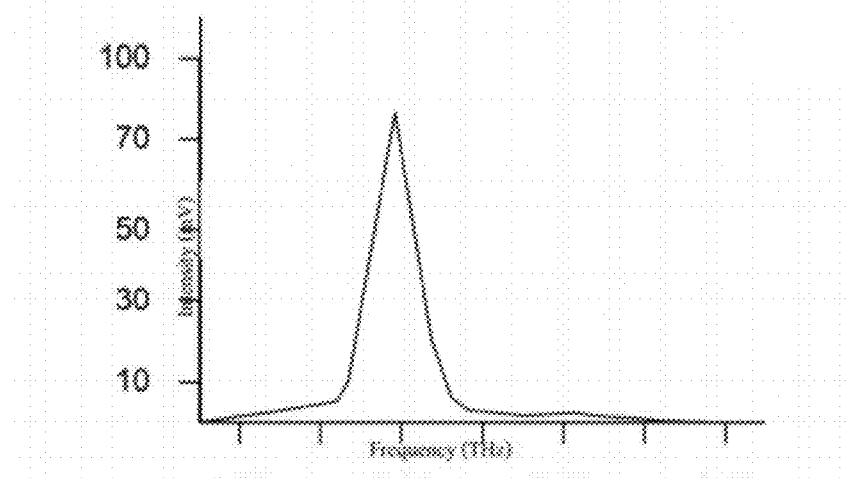
FIG. 5C shows an intensity versus frequency graph depicting use of inverse Hilbert Transforms on YCBO Josephson junction detector response.

As discussed above, the preferred detector consists of an unpowered High-($T_c$) YBCO Josephson junction which is kept at liquid nitrogen temperature and which develops voltage across its junction in a complex relationship to the reflected Terahertz frequency. The intensity versus voltage graph is then plotted as shown in FIGS. 5A and 5B. This graph is converted to intensity versus frequency FIG. 5C using inverse Hilbert Transforms. The rotational frequencies corresponding to a typical explosive will then be present on this graph. For instance, if the subject is carrying RDX on his body, the detector will respond to specific reflected frequencies which will include 0.82, 1.05, 1.50, 1.96, and 2.20 THz. Other frequencies will also be present but may not be as dominant. Likewise, PETN will reflect frequencies of waves at 2.0 and 2.84 THz. Semtex, which is a mixture of RDX, PETN, and a plasticizer, will have response at 0.82, 1.05, 1.50, 1.96, 2.0, 2.20, and 2.84 THz, which is a union of the responses of RDX and PETN. Some of these frequencies are quite close; however, Josephson junctions can resolve these readily. An electronic library of the spectral responses of all explosives preferably can be compiled for identification of specific explosives.

Alternatively, instead of calculating the inverse Hilbert Transform of the voltage developed in the YCBO Josephson junction detector, a quick method for identifying the explosives is presented based on the voltage developed in the detector. The relationship between the voltage and frequency is given by $$V = \frac{\hbar}{2e} f:$$

where $\hbar$ is Plank's constant divided by $2\pi$ and e is the electronic charge. With reference now to FIG. 4, a table of common explosives and their voltage specific signatures is provided.

Figure 6A:
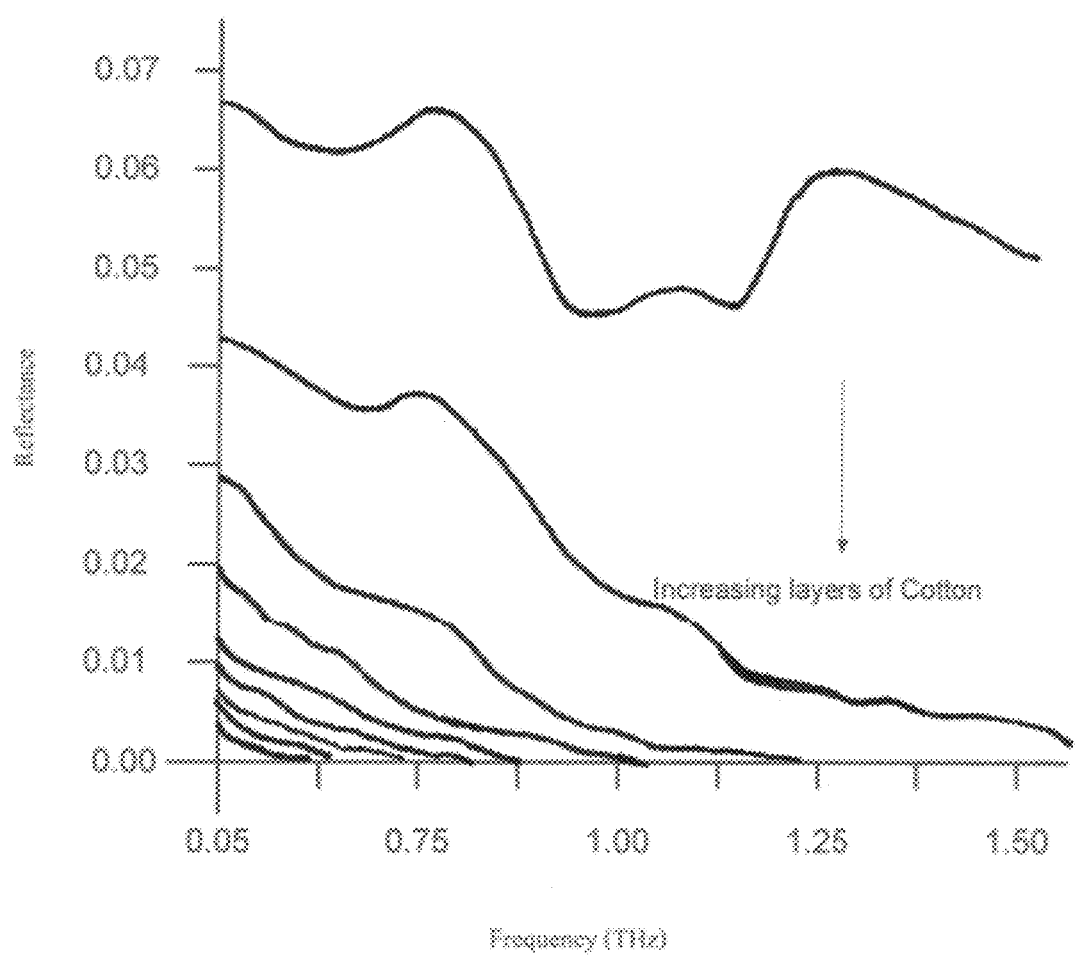
FIG. 6A shows the reflectance versus frequency of an explosive behind cotton cloth barrier as disclosed in prior art.
Figure 6B:
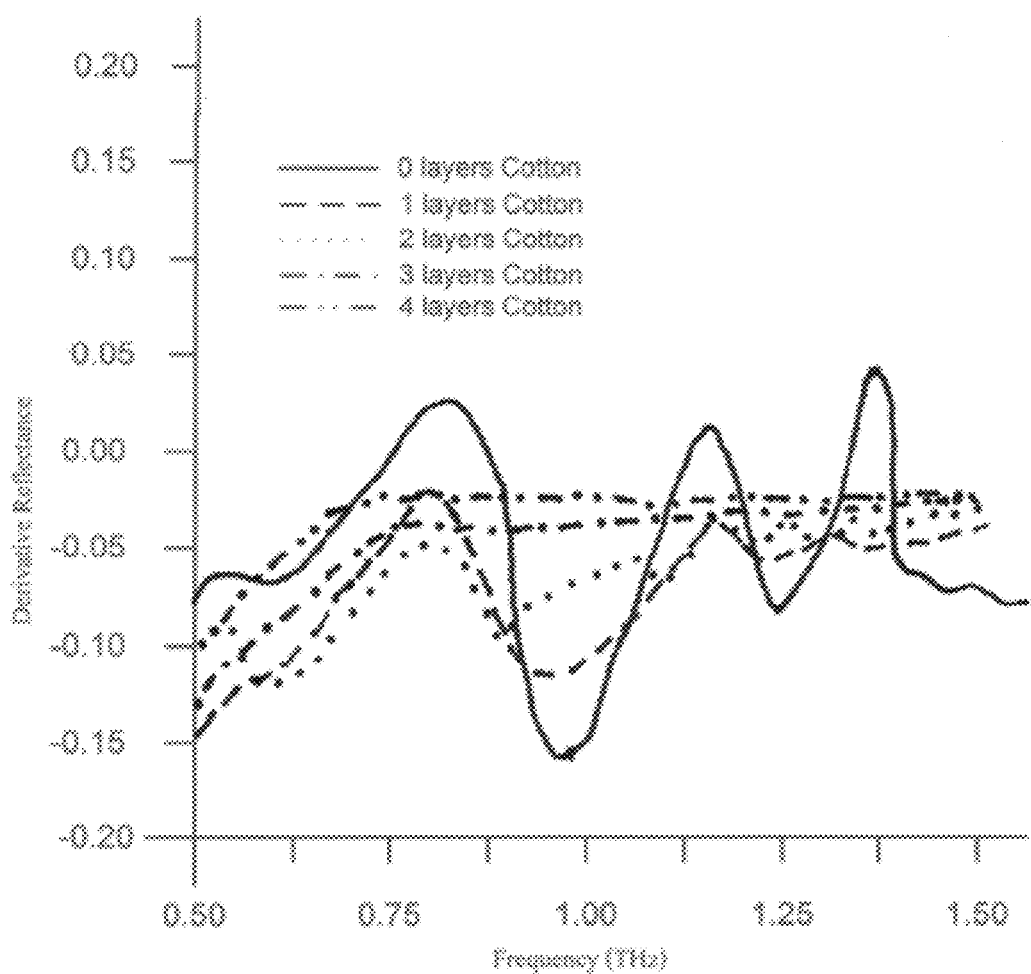
FIG. 6B shows the derivative of reflectance versus frequency of an explosive as disclosed in prior art.

With reference now to FIGS. 6A and 6B as disclosed in Baker et al., "Detection of Concealed Explosives at a Distance Using Terahertz Technology", Proc IEEE, Vol. 95, No. 8, August 2007, pp. 1559-1565, the effect of clothing on the spectral image will now be discussed. As shown in FIG. 6A, the presence of clothing tends to smear the frequency response of the explosive, blurring the well-defined peaks and reducing the intensity. As shown in FIG. 6B, with the use of a mathematical technique, differentiation with respect to frequency may be employed to sharpen the peaks when the peak blurring occurs due to signal propagation in mediums such as water vapor or clothing. The false alarm rate of detection is considerably reduced by this technique.

Figure 6C:
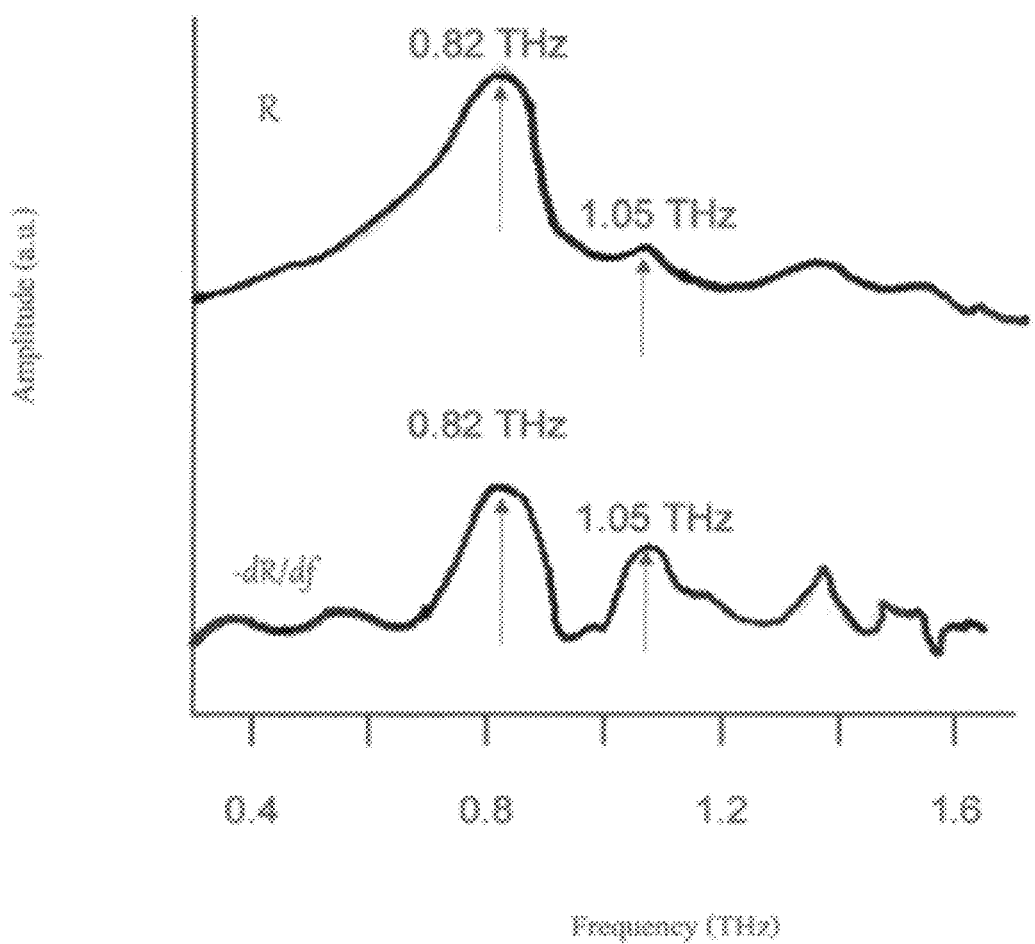
FIG. 6C shows mathematical differentiation of amplitude versus frequency derived from multiple detectors of RDX explosive as disclosed in prior art.

With reference to FIG. 6C, an example for RDX detection as disclosed in Zhong et al., "Identification and classification of chemicals using Terahertz reflective spectroscopic focal plane imaging system", Optical Express, Vol. 14, No. 20, 2 Oct. 2006, will now be discussed. The peaks corresponding to THz absorption of RDX are shown in the top half of the graph. The bottom half shows the derivative of reflectance with respect to frequency. The same peaks are present in both plots. Notably, Zhong derived the resultant graphs of FIG. 6C using Zinc Telluride (ZnTe) to detect and a CCD camera to image, not Josephson junctions. ZnTe is not as sensitive as Josephson junctions and the imaging requires a substantially longer duration of time.

This process of differentiation tends to restore the sharpness of the peaks. Differentiation can be carried out repeatedly (e.g. $d^2R/df^2$) until it is ascertained that the reflected THz has no features indicative of an explosive. The use of reflectance rather than reflected energy is used here; the normalized results facilitate comparison of two separate detectors and/or responses of the same detector at two frequencies.

In a preferred embodiment of the present invention, the source 272, a BSCCO Josephson junction is located together with the YCBO Josephson junction detector 276 in the same liquid nitrogen Dewar. The voltage of the BSCCO Josephson junction is increased from 1 mV to 10 mV and then decreased from 10 mV back to 1 mV in a continuous manner. The power cycle repeats itself at a predetermined rate. As a result, the Josephson junction emits frequencies from 0.5 to 5 THz which emanate from the top surface of BSCCO. The Terahertz radiation propagates mostly in the forward direction. Since these frequencies are readily absorbed by water vapors present in air, they cannot propagate very far. However, if someone is carrying an explosive on his body and is in the vicinity of source/detector system, enough Terahertz radiation will transmit or diffusively scatter through the clothing, partially reflected by the explosive and skin, then scatter through the clothing once again and be received by the detector, which will develop voltage in accordance with the reflected frequencies of the explosive.

Figure 7:
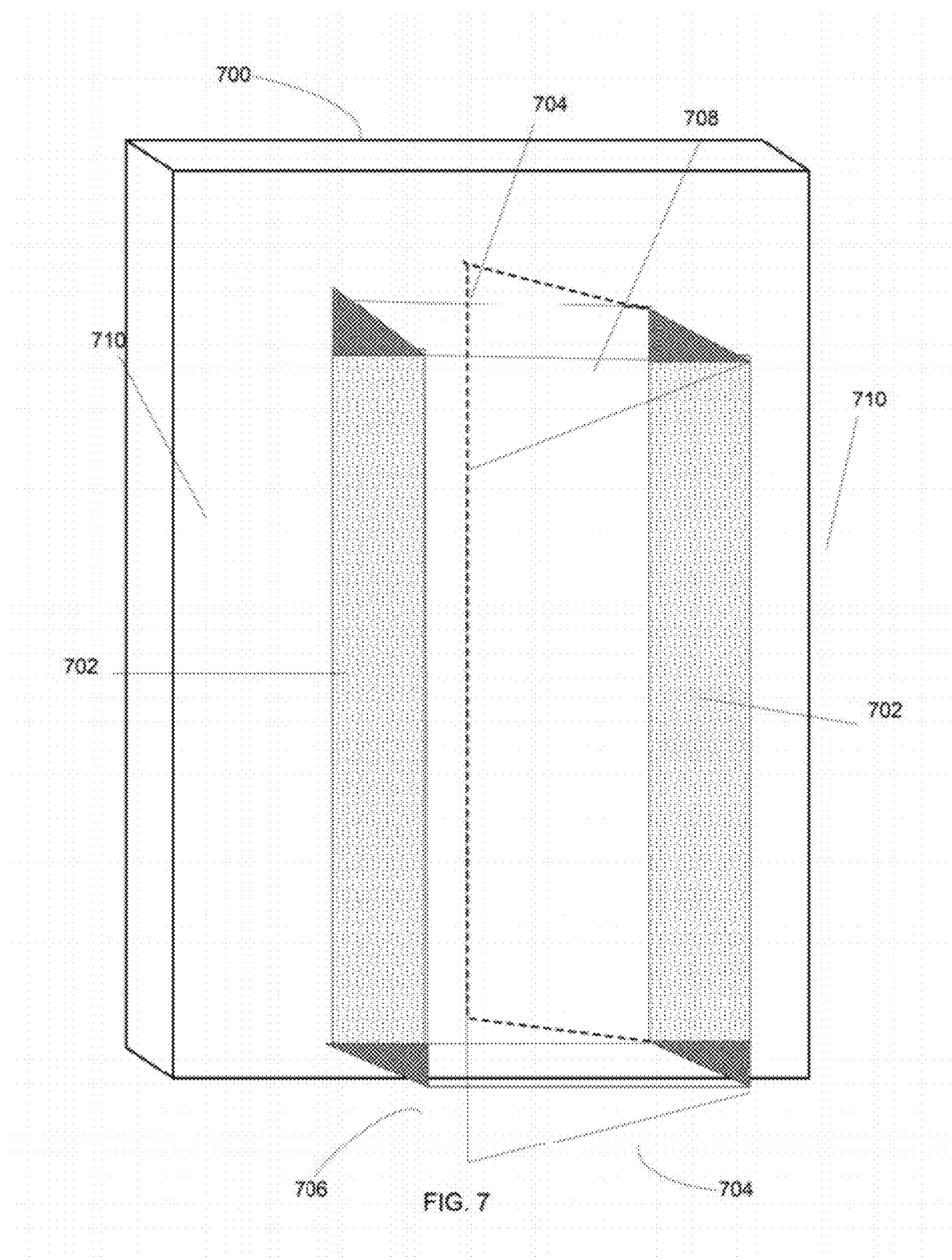
FIG. 7 shows a third preferred embodiment of the present invention.

With reference now to FIG. 7, a preferred embodiment of the present invention will be further discussed. As shown, a portal constitutes two sidewalls 702, two open doors 704, a floor 706 and a ceiling 708 of a chamber for investigating a subject. The opening doors 704 facing each other are for easy entry and easy exit of the subject under investigation. The two sidewalls 702 have circular apertures arranged in a two dimensional grid consisting of several row and columns. In order to cover the entire human body on two sides, head and feet, a multitude of apertures are provided. Inside each aperture a convex lens (size 1") made from polyethylene is provided. The dimensions of the portal and the position of the walls are so arranged that an average adult can stand comfortably with no body part more than a distance of 10"-12" from either wall. Viewing from two sides can give fairly good indication of a concealed package strapped on a human body. The portal is enclosed in a bomb proof room 710 to reduce the effect of any blast or shrapnel resulting from an explosive detonation.

According to a preferred embodiment of the present invention, a plurality of elements comprising emitters 276 and detectors 272 are arranged in a rectangular grid; the vertical columns of the grid will be parallel to the height of the subject and the horizontal rows of elements will correspond to the width of the subject. An arrangement like this can be located on the opposite walls of a confinement for obtaining the explosive spectrum from both sides of the human body.

In an alternative embodiment of the present invention, the coverage in the vertical direction is obtained by locating the elements comprising emitters 272 and detectors 276 on a single vertical line while the horizontal coverage is obtained by employing a combination of alternating current and magnets. The beam from each detector is steered from one side to the other, sweeping an arc of a circle in the horizontal plane. The scan of the whole human body is thus obtained by such an arrangement and the fingerprints of explosive will be captured if present.

Figure 8:
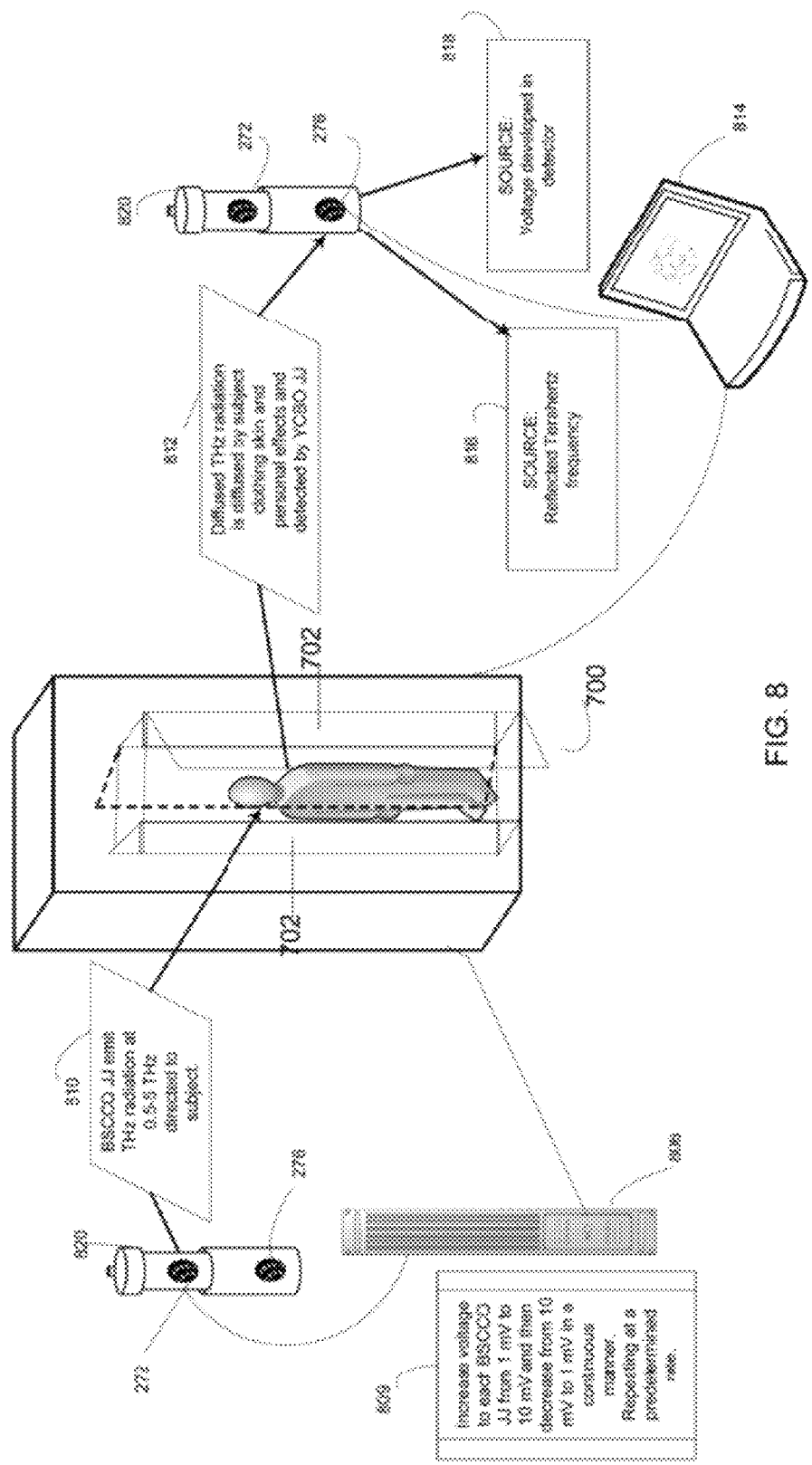
FIG. 8 shows a system diagram of an embodiment of the invention.

With reference now to FIG. 8, an exemplary system and method incorporating the present invention will now be discussed. According to a preferred embodiment 802, the liquid nitrogen Dewar emitter/detector units 820 are preferably arranged in a rectangular grid contained in both the opposite walls 702 of the portal booth 700 in a manner in which all body parts of the subject are within 10-12" from either wall. Further, a power source 806 is provided and configured to send voltage to each emitter 276. Preferably, the voltage may be adjusted 1 mV to 10 mV and then decreased from 10 mV to 1 mV in a continuous manner at a predetermined rate and pattern 809. The BSCCO Josephson junctions 272 emit THz radiation at 0.5-5 THz directed to the subject 810.

The THz radiation may be diffused by the subject's clothing, skin, and personal effects and is preferably detected by the unpowered YCBO Josephson junction detectors 272. The detectors 272 are preferably monitored by a computer 814 programmed to decipher the THz radiation of the YCBO Josephson junctions 272 using alternative functions which results in positive identification of explosives and/or explosive materials. The first method of detection may be based on the frequency of the reflected THz radiation 816 from the detector 272. The reflected THz frequency may be graphed with respect to the voltage and this graph may be converted to intensity versus frequency using inverse Hilbert Transform. Preferably, differentiation with respect to frequency may be employed to sharpen the peaks when blurring occurs due to signal propagation after which the spectral response may be compared to the spectral responses of known explosives. Preferably, this reading is collected and contrasted to the data of two or more detectors or the same detector at different frequencies. Computer data may be monitored on-site or remotely preferably in real-time to ensure rapid response time. Differentiation with respect to frequency will sharpen the peaks as described previously.

A second preferred method of detection may be based on monitoring the voltage developed in the detector by the THz radiation 818 and comparing the recorded voltage to specific signatures of known explosives as shown in FIG. 4. Likewise, computer data may be monitored on-site or remotely preferably in real-time to ensure rapid response time.

In a second alternate embodiment of the present invention, Embodiment B 804, emitter/detector units 820 may be arranged in a single vertical line parallel to the subject's height. In this alternate embodiment the horizontal width of the subject may be irradiated by THz radiation steered by alternating current and magnets which may create a beam. This beam may preferably be steered in a circular arc in the horizontal plane. This arrangement of a single vertical column of emitter/detector units 820 may be confined to one wall 702 in the portal booth 700 or positioned in each opposing wall 702 in the portal booth 700.

In a third alternate embodiment, the present invention may be employed where the portal booth 700 is also equipped with a rotating platform to further ensure complete coverage of the subject in the portal booth 700.

The example discussed above highlights the use of High-$T_c$ Josephson junction in security check point portals; the system can be equally well incorporated at revolving entrance doors, moving walkways, escalators, jetways and airport doors. Alternatively, implementation of High-$T_c$ Josephson junction based source/detector system in auxiliary viewing points can do away with the highly inconvenient security portals altogether. One set or several can be incorporated in each of the inspection sites. The beam emanating from BSCCO Josephson junction can be steered from one part of the body to the other using magnets as described by Welp et al. A plurality of Josephson junctions can be incorporated into the walls, ceilings and floor of the portals to make quick and unambiguous detection of the explosives.

As detailed herein, the present invention provides a reliable means of generating Terahertz waves and detecting reflected Terahertz waves to detect and confirm the presence of explosives. Furthermore, real time explosive signatures can be derived from the information contained in the reflected Terahertz waves using innovative mathematical techniques to consistently yield accurate and reliable detection of explosives without raising privacy concerns.

While the above description contains much specificity, these should not be construed as limitations on the scope, but rather as examples. Many other variations are possible.

Accordingly, the scope should be determined not by the embodiments illustrated, but by the appended claims and their legal equivalents.

I claim:

1. A method for detecting the presence of explosives on a target, the method comprising:
   a) providing an emitter containing a BSCCO Josephson junction stack, wherein the emitter is configured to direct terahertz radiation against a target;
   b) adjusting the voltage across the BSCCO Josephson junction stacks from 1 mV to 10 mV and back to 1 mV at a predetermined rate to produce THz at 0.5 GHz to 5.0 THz frequencies;
   c) providing a detector, wherein the detector is comprised of at least one YCBO Josephson junction detector for receiving terahertz radiation reflected from the target;
   d) converting frequency measurements of the reflected radiation by inverse Hilbert Transform; and
   e) analyzing the reflected radiation received by the detector to identify explosive.

2. An apparatus for detecting the presence of explosives on a target, the apparatus comprising:
   a) an emitter containing a BSCCO Josephson junction stack, wherein the emitter is configured to adjust the voltage across the BSCCO Josephson junction stacks from 1 mV to 10 mV and back to 1 mV at a predetermined rate and direct terahertz radiation against a target;
   b) a detector, wherein the detector is comprised of at least one YCBO Josephson junction detector for receiving terahertz radiation reflected from the target; and
   c) a computing element configured to analyze the reflected radiation received by the detector to identify explosives by employment of at least a first and second derivative of the reflectance of the radiation over the entire spectral response of the explosive.

3. An apparatus for detecting the presence of explosives on a target, the apparatus comprising:
   a) an emitter containing a BSCCO Josephson junction stack, wherein the emitter is configured to adjust the voltage across the BSCCO Josephson junction stacks from 1 mV to 10 mV and back to 1 mV at a predetermined rate and direct terahertz radiation against a target;
   b) a detector, wherein the detector is comprised of at least one YCBO Josephson junction detector for receiving terahertz radiation reflected from the target; and
   c) a computing element configured to analyze the reflected radiation received by the detector to identify explosives by employment of at least a first and second derivative of the reflectance of the radiation over the entire spectral response of the explosive, and further wherein the computing element is configured to combine and analyze data from one detector at two different frequencies for obtaining an explosive signature.

* * * * *